US012144566B2

(12) United States Patent
Birenbaum et al.

(10) Patent No.: US 12,144,566 B2
(45) Date of Patent: *Nov. 19, 2024

(54) SYSTEM AND METHOD FOR CATHETER DETECTION IN FLUOROSCOPIC IMAGES AND UPDATING DISPLAYED POSITION OF CATHETER

(71) Applicant: Covidien LP, Mansfield, MA (US)

(72) Inventors: Ariel Birenbaum, Raanana (IL); Ron Barak, Tel Aviv (IL); Oren P. Weingarten, Hod-Hasharon (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,924

(22) Filed: Jun. 7, 2023

(65) Prior Publication Data
US 2023/0310093 A1 Oct. 5, 2023

Related U.S. Application Data

(63) Continuation of application No. 17/584,039, filed on Jan. 25, 2022, now Pat. No. 11,701,184, which is a
(Continued)

(51) Int. Cl.
*A61B 6/03* (2006.01)
*A61B 6/00* (2006.01)
(Continued)

(52) U.S. Cl.
CPC .............. *A61B 34/20* (2016.02); *A61B 6/025* (2013.01); *A61B 6/032* (2013.01); *A61B 6/12* (2013.01);
(Continued)

(58) Field of Classification Search
CPC ..... A61B 6/00; A61B 6/02; A61B 2034/2051; A61B 6/12; A61B 6/487; A61B 34/20;
(Continued)

(56) References Cited

U.S. PATENT DOCUMENTS 5,706,324 A 1/1998 Wiesent et al.
5,852,646 A 12/1998 Klotz et al.
(Continued)

FOREIGN PATENT DOCUMENTS

BR 0013237 A 7/2003
BR 0116004 A 6/2004
(Continued)

OTHER PUBLICATIONS

Australian Examination Report No. 2 issued in Appl. No. AU 2016210747 dated Oct. 18, 2017 (4 pages).
(Continued)

*Primary Examiner* — Tuan H Nguyen
(74) *Attorney, Agent, or Firm* — Weber Rosselli & Cannon LLP

(57) ABSTRACT

A method and system implementing a method for detecting a catheter in fluoroscopic data and updating a displayed electromagnetic position of the catheter on a 3D rendering is provided including navigating a catheter to a target area and acquiring fluoroscopic data from a fluoroscopic sweep of the target area. An initial catheter detection is performed to detect catheter tip candidates in each 2D frame of the fluoroscopic data using a shallow neural network. A secondary catheter detection is performed to detect catheter tip candidates in each 2D frame of the fluoroscopic data using a deep neural network. False-positive catheter tip candidates are removed by reconstructing a 3D position of the catheter tip and finding an intersecting point of rays corresponding to each 2D frame.

20 Claims, 7 Drawing Sheets

Related U.S. Application Data continuation of application No. 17/115,589, filed on Dec. 8, 2020, now Pat. No. 11,253,325, which is a continuation of application No. 16/259,731, filed on Jan. 28, 2019, now Pat. No. 10,905,498.

(60) Provisional application No. 62/627,911, filed on Feb. 8, 2018.

(51) Int. Cl.
| | |
|---|---|
| A61B 6/02 | (2006.01) |
| A61B 6/12 | (2006.01) |
| A61B 6/46 | (2024.01) |
| A61B 34/20 | (2016.01) |
| A61B 5/06 | (2006.01) |
| A61B 90/00 | (2016.01) |

(52) U.S. Cl.
CPC .............. *A61B 6/465* (2013.01); *A61B 6/466* (2013.01); *A61B 6/487* (2013.01); *A61B 6/5205* (2013.01); *A61B 5/061* (2013.01); *A61B 6/5235* (2013.01); *A61B 2034/2051* (2016.02); *A61B 90/37* (2016.02); *A61B 2090/376* (2016.02)

(58) Field of Classification Search
CPC ......... A61B 6/466; A61B 6/025; A61B 6/032; A61B 6/5205; A61B 5/061; A61B 6/465; A61B 6/03
See application file for complete search history.

(56) References Cited

U.S. PATENT DOCUMENTS

| | | | |
|---|---|---|---|
| 5,930,329 | A | 7/1999 | Navab |
| 5,951,475 | A | 9/1999 | Gueziec et al. |
| 5,963,612 | A | 10/1999 | Navab |
| 5,963,613 | A | 10/1999 | Navab |
| 6,038,282 | A | 3/2000 | Wiesent et al. |
| 6,049,582 | A | 4/2000 | Navab |
| 6,050,724 | A | 4/2000 | Schmitz et al. |
| 6,055,449 | A | 4/2000 | Navab |
| 6,081,577 | A | 6/2000 | Webber |
| 6,118,845 | A | 9/2000 | Simon et al. |
| 6,120,180 | A | 9/2000 | Graumann |
| 6,236,704 | B1 | 5/2001 | Navab et al. |
| 6,243,439 | B1 | 6/2001 | Arai et al. |
| 6,285,739 | B1 | 9/2001 | Rudin et al. |
| 6,289,235 | B1 | 9/2001 | Webber et al. |
| 6,317,621 | B1 | 11/2001 | Graumann et al. |
| 6,351,513 | B1 | 2/2002 | Bani-Hashemi et al. |
| 6,359,960 | B1 | 3/2002 | Wahl et al. |
| 6,382,835 | B2 | 5/2002 | Graumann et al. |
| 6,389,104 | B1 | 5/2002 | Bani-Hashemi et al. |
| 6,404,843 | B1 | 6/2002 | Vaillant |
| 6,424,731 | B1 | 7/2002 | Launay et al. |
| 6,484,049 | B1 | 11/2002 | Seeley et al. |
| 6,485,422 | B1 | 11/2002 | Mikus et al. |
| 6,490,475 | B1 | 12/2002 | Seeley et al. |
| 6,491,430 | B1 | 12/2002 | Seissler |
| 6,546,068 | B1 | 4/2003 | Shimura |
| 6,546,279 | B1 | 4/2003 | Bova et al. |
| 6,549,607 | B1 | 4/2003 | Webber |
| 6,585,412 | B2 | 7/2003 | Mitschke |
| 6,662,036 | B2 | 12/2003 | Cosman |
| 6,666,579 | B2 | 12/2003 | Jensen |
| 6,697,664 | B2 | 2/2004 | Kienzle et al. |
| 6,707,878 | B2 | 3/2004 | Claus et al. |
| 6,714,810 | B2 | 3/2004 | Grzeszczuk et al. |
| 6,731,283 | B1 | 5/2004 | Navab |
| 6,731,970 | B2 | 5/2004 | Schlossbauer et al. |
| 6,768,784 | B1 | 7/2004 | Green et al. |
| 6,782,287 | B2 | 8/2004 | Grzeszczuk et al. |
| 6,785,356 | B2 | 8/2004 | Grass et al. |
| 6,785,571 | B2 | 8/2004 | Glossop |
| 6,801,597 | B2 | 10/2004 | Webber |
| 6,810,278 | B2 | 10/2004 | Webber et al. |
| 6,823,207 | B1 | 11/2004 | Jensen et al. |
| 6,851,855 | B2 | 2/2005 | Mitschke et al. |
| 6,856,826 | B2 | 2/2005 | Seeley et al. |
| 6,856,827 | B2 | 2/2005 | Seeley et al. |
| 6,865,253 | B2 | 3/2005 | Blumhofer et al. |
| 6,898,263 | B2 | 5/2005 | Avinash et al. |
| 6,912,265 | B2 | 6/2005 | Hebecker et al. |
| 6,928,142 | B2 | 8/2005 | Shao et al. |
| 6,944,260 | B2 | 9/2005 | Hsieh et al. |
| 6,956,927 | B2 | 10/2005 | Sukeyasu et al. |
| 7,010,080 | B2 | 3/2006 | Mitschke et al. |
| 7,010,152 | B2 | 3/2006 | Bojer et al. |
| 7,035,371 | B2 | 4/2006 | Boese et al. |
| 7,048,440 | B2 | 5/2006 | Graumann et al. |
| 7,066,646 | B2 | 6/2006 | Pescatore et al. |
| 7,106,825 | B2 | 9/2006 | Gregerson et al. |
| 7,117,027 | B2 | 10/2006 | Zheng et al. |
| 7,129,946 | B2 | 10/2006 | Ditt et al. |
| 7,130,676 | B2 | 10/2006 | Barrick |
| 7,142,633 | B2 | 11/2006 | Eberhard et al. |
| 7,147,373 | B2 | 12/2006 | Cho et al. |
| 7,165,362 | B2 | 1/2007 | Jobs et al. |
| 7,186,023 | B2 | 3/2007 | Morita et al. |
| 7,251,522 | B2 | 7/2007 | Essenreiter et al. |
| 7,327,872 | B2 | 2/2008 | Vaillant et al. |
| 7,343,195 | B2 | 3/2008 | Strommer et al. |
| 7,369,641 | B2 | 5/2008 | Tsubaki et al. |
| 7,426,256 | B2 | 9/2008 | Rasche et al. |
| 7,440,538 | B2 | 10/2008 | Tsujii |
| 7,467,007 | B2 | 12/2008 | Lothert |
| 7,474,913 | B2 | 1/2009 | Durlak |
| 7,502,503 | B2 | 3/2009 | Bojer et al. |
| 7,505,549 | B2 | 3/2009 | Ohishi et al. |
| 7,508,388 | B2 | 3/2009 | Barfuss et al. |
| 7,603,155 | B2 | 10/2009 | Jensen et al. |
| 7,620,223 | B2 | 11/2009 | Xu et al. |
| 7,639,866 | B2 | 12/2009 | Pomero et al. |
| 7,664,542 | B2 | 2/2010 | Boese et al. |
| 7,671,887 | B2 | 3/2010 | Pescatore et al. |
| 7,689,019 | B2 | 3/2010 | Boese et al. |
| 7,689,042 | B2 | 3/2010 | Brunner et al. |
| 7,693,263 | B2 | 4/2010 | Bouvier et al. |
| 7,711,082 | B2 | 5/2010 | Fujimoto et al. |
| 7,711,083 | B2 | 5/2010 | Heigl et al. |
| 7,711,409 | B2 | 5/2010 | Keppel et al. |
| 7,712,961 | B2 | 5/2010 | Horndler et al. |
| 7,720,520 | B2 | 5/2010 | P et al. |
| 7,725,165 | B2 | 5/2010 | Chen et al. |
| 7,734,329 | B2 | 6/2010 | Boese et al. |
| 7,742,557 | B2 | 6/2010 | Brunner et al. |
| 7,761,135 | B2 | 7/2010 | Pfister et al. |
| 7,778,685 | B2 | 8/2010 | Evron et al. |
| 7,778,690 | B2 | 8/2010 | Boese et al. |
| 7,787,932 | B2 | 8/2010 | Vilsmeier et al. |
| 7,804,991 | B2 | 9/2010 | Abovitz et al. |
| 7,831,096 | B2 | 11/2010 | Williamson et al. |
| 7,835,779 | B2 | 11/2010 | Anderson et al. |
| 7,844,094 | B2 | 11/2010 | Jeung et al. |
| 7,853,061 | B2 | 12/2010 | Gorges et al. |
| 7,877,132 | B2 | 1/2011 | Rongen et al. |
| 7,899,226 | B2 | 3/2011 | Pescatore et al. |
| 7,907,989 | B2 | 3/2011 | Borgert et al. |
| 7,912,180 | B2 | 3/2011 | Zou et al. |
| 7,912,262 | B2 | 3/2011 | Timmer et al. |
| 7,949,088 | B2 | 5/2011 | Nishide et al. |
| 7,950,849 | B2 | 5/2011 | Claus et al. |
| 7,991,450 | B2 | 8/2011 | Virtue et al. |
| 8,000,436 | B2 | 8/2011 | Seppi et al. |
| 8,043,003 | B2 | 10/2011 | Vogt et al. |
| 8,045,780 | B2 | 10/2011 | Boese et al. |
| 8,050,739 | B2 | 11/2011 | Eck et al. |
| 8,090,168 | B2 | 1/2012 | Washburn et al. |
| 8,104,958 | B2 | 1/2012 | Weiser et al. |
| 8,111,894 | B2 | 2/2012 | Haar |
| 8,111,895 | B2 | 2/2012 | Spahn |
| 8,126,111 | B2 | 2/2012 | Uhde et al. |

(56) References Cited

U.S. PATENT DOCUMENTS

| | | |
|---|---|---|
| 8,126,241 B2 | 2/2012 | Zarkh et al. |
| 8,150,131 B2 | 4/2012 | Harer et al. |
| 8,180,132 B2 | 5/2012 | Gorges et al. |
| 8,195,271 B2 | 6/2012 | Rahn |
| 8,200,316 B2 | 6/2012 | Keppel et al. |
| 8,208,708 B2 | 6/2012 | Homan et al. |
| 8,229,061 B2 | 7/2012 | Hanke et al. |
| 8,248,413 B2 | 8/2012 | Gattani et al. |
| 8,270,691 B2 | 9/2012 | Xu et al. |
| 8,271,068 B2 | 9/2012 | Khamene et al. |
| 8,275,448 B2 | 9/2012 | Camus et al. |
| 8,306,303 B2 | 11/2012 | Bruder et al. |
| 8,311,617 B2 | 11/2012 | Keppel et al. |
| 8,320,992 B2 | 11/2012 | Frenkel et al. |
| 8,326,403 B2 | 12/2012 | Pescatore et al. |
| 8,335,359 B2 | 12/2012 | Fidrich et al. |
| 8,340,379 B2 | 12/2012 | Razzaque et al. |
| 8,345,817 B2 | 1/2013 | Fuchs et al. |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,184 B2 | 4/2014 | Mohr et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,827,934 B2 | 9/2014 | Chopra et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,401,047 B2 | 7/2016 | Bogoni et al. |
| 9,406,134 B2 | 8/2016 | Klingenbeck-Regn et al. |
| 9,445,772 B2 | 9/2016 | Callaghan et al. |
| 9,445,776 B2 | 9/2016 | Han et al. |
| 9,466,135 B2 | 10/2016 | Koehler et al. |
| 9,743,896 B2 | 8/2017 | Averbuch |
| 9,918,659 B2 | 3/2018 | Chopra et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 10,905,498 B2 | 2/2021 | Birenbaum et al. |
| 2002/0122536 A1 | 9/2002 | Kerrien et al. |
| 2002/0163996 A1 | 11/2002 | Kerrien et al. |
| 2002/0188194 A1 | 12/2002 | Cosman |
| 2003/0013972 A1 | 1/2003 | Makin |
| 2003/0088179 A1 | 5/2003 | Seeley et al. |
| 2005/0220264 A1 | 10/2005 | Homegger |
| 2005/0245807 A1 | 11/2005 | Boese et al. |
| 2005/0281385 A1 | 12/2005 | Johnson et al. |
| 2006/0182216 A1 | 8/2006 | Lauritsch et al. |
| 2006/0251213 A1 | 11/2006 | Bernhardt et al. |
| 2007/0276216 A1 | 11/2007 | Beyar et al. |
| 2013/0223702 A1* | 8/2013 | Holsing ............... A61B 5/061 382/128 |
| 2013/0303945 A1 | 11/2013 | Blumenkranz et al. |
| 2014/0035798 A1 | 2/2014 | Kawada et al. |
| 2014/0275985 A1* | 9/2014 | Walker ............... A61B 5/062 606/130 |
| 2015/0148690 A1 | 5/2015 | Chopra et al. |
| 2015/0227679 A1 | 8/2015 | Kamer et al. |
| 2015/0265368 A1 | 9/2015 | Chopra et al. |
| 2016/0005194 A1 | 1/2016 | Schretter et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0206380 A1 | 7/2016 | Sparks et al. |
| 2016/0287343 A1 | 10/2016 | Eichler et al. |
| 2016/0287344 A1 | 10/2016 | Donhowe et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |

(56) References Cited

U.S. PATENT DOCUMENTS

| | | |
|---|---|---|
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CN | 101190149 A | 6/2008 |
| CZ | 486540 B1 | 9/2016 |
| CZ | 2709512 B6 | 8/2017 |
| CZ | 2884879 B1 | 1/2020 |
| DE | 19919907 A1 | 11/2000 |
| DE | 69726415 T | 9/2004 |
| DE | 102004004620 A1 | 8/2005 |
| EP | 0917855 A1 | 5/1999 |
| EP | 1593343 A2 | 11/2005 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |
| WO | 9944503 A1 | 9/1999 |
| WO | 0187136 A2 | 11/2001 |
| WO | 2004081877 A1 | 9/2004 |
| WO | 2005015125 A1 | 2/2005 |
| WO | 2005082246 A1 | 9/2005 |
| WO | 2009081297 A2 | 7/2009 |
| WO | 2015101948 A2 | 7/2015 |

OTHER PUBLICATIONS

Canadian Office Action issued in Appl. No. 2,937,825 dated Mar. 26, 2018 (4 pages).

CT scan—Wikipedia, the free encyclopedia [retrieved from internet on Mar. 30, 2017]. published on Jun. 30, 2015 as per Wayback Machine.

Extended European Search Report from Appl. No. EP 16182953. 6-1666 dated Jan. 2, 2017.

Extended European Search Report issued in corresponding Appl. No. EP 19156034.1 dated Jul. 8, 2019 (10 pages).

Extended European search report issued in European Patent Application No. 22188667.4 dated Nov. 7, 2022.

Lee, Flyunkwang, et al., "A Deep-Learning System for Fully-Automated Peripherally Inserted Central Catheter (PICC) Tip Detection", J. Digit Imaging, vol. 31, pp. 393-402 (2018).

Office Action issued in Chinese Appl. No. 201610635896.X dated Jul. 23, 2018, together with English language translation (16 pages).

* cited by examiner

SYSTEM AND METHOD FOR CATHETER DETECTION IN FLUOROSCOPIC IMAGES AND UPDATING DISPLAYED POSITION OF CATHETER

CROSS-REFERENCE TO RELATED APPLICATIONS

This application is a continuation of U.S. patent application Ser. No. 17/584,039, filed on Jan. 25, 2022, which is a continuation of U.S. patent application Ser. No. 17/115,589, filed on Dec. 8, 2020, now U.S. Pat. No. 11,253,325, which is a continuation of U.S. patent application Ser. No. 16/259,731, filed on Jan. 28, 2019, now U.S. Pat. No. 10,905,498, which claims the benefit of the filing date of provisional U.S. Patent Application Ser. No. 62/627,911, filed on Feb. 8, 2018, the entire contents of each of which are incorporated herein by reference.

BACKGROUND

The disclosure relates to a system, apparatus, and method of detecting a catheter in a series of fluoroscopic images, determining the position of the catheter based on the detection, and updating the displayed position of the catheter in an electromagnetic navigation system for surgical procedures.

There are several commonly applied methods for treating various maladies affecting organs including the liver, brain, heart, lung and kidney. Often, one or more imaging modalities, such as magnetic resonance imaging, ultrasound imaging, computed tomography (CT), as well as others are employed by clinicians to identify areas of interest within a patient and ultimately targets for treatment.

An endoscopic approach has proven useful in navigating to areas of interest within a patient, and particularly so for areas within luminal networks of the body such as the lungs. To enable the endoscopic, and more particularly the bronchoscopic, approach in the lungs, endobronchial navigation systems have been developed that use previously acquired MRI data or CT image data to generate a three dimensional rendering or volume of the particular body part such as the lungs. In particular, previously acquired images, acquired from an MRI scan or CT scan of the patient, are utilized to generate a three dimensional or volumetric rendering of the patient.

The resulting volume generated from the MRI scan or CT scan is then utilized to create a navigation plan to facilitate the advancement of a navigation catheter (or other suitable device) through a bronchoscope and a branch of the bronchus of a patient to an area of interest. Electromagnetic tracking may be utilized in conjunction with the CT data to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

A fluoroscopic imaging device is commonly located in the operating room during navigation procedures. The standard fluoroscopic imaging device may be used by a clinician to visualize and confirm the placement of a tool after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions or tumors. Further, the fluoroscope image is only a two dimensional projection. In order to be able to see small soft-tissue objects in three dimensional space, an X-ray volumetric reconstruction is needed. Several solutions exist that provide three dimensional volume reconstruction of soft-tissues such as CT and Cone-beam CT which are extensively used in the medical world. These machines algorithmically combine multiple X-ray projections from known, calibrated X-ray source positions into three dimensional volume in which the soft-tissues are visible.

SUMMARY

The disclosure relates to a system, apparatus, and method of detecting a catheter in a series of fluoroscopic images, determining the position of the catheter based on the detection, and updating the displayed position of the catheter in an electromagnetic navigation system for surgical procedures. The disclosure utilizes a combination of shallow neural network operators and deep neural network operators to detect catheter candidates in a fluoroscopic data set. Additionally, false-positive candidate detections are eliminated according to the methods described herein. The position data of the catheter is acquired from the fluoroscopic data and is used as a correction factor for the displayed electromagnetically tracked position of the catheter.

The system of the disclosure constructs a fluoroscopic-based 3D construction of a target area which includes the catheter and a target (e.g., soft-tissue object, lesion, tumor, etc.) in order to determine the location of the catheter relative to the target. In particular, the system identifies the position, orientation, angle, and distance of the catheter relative to the target in each fluoroscopic frame of the fluoroscopic data. This relative location data is used to update a displayed electromagnetic position of the catheter over a CT-based rendering, for example, of a patient's luminal network. With this updated display, a clinician is able to more accurately navigate and confirm placement of the catheter and other surgical tools relative to a target during an electromagnetic navigation procedure.

Aspects of the disclosure are described in detail with reference to the figures wherein like reference numerals identify similar or identical elements. As used herein, the term "distal" refers to the portion that is being described which is further from a user, while the term "proximal" refers to the portion that is being described which is closer to a user.

According to one aspect of the disclosure, a method for detecting a catheter in fluoroscopic data is provided. The method includes acquiring fluoroscopic data from a fluoroscopic sweep of a target area. The target area may be, for example, within a patient's luminal network. The fluoroscopic data includes 2D fluoroscopic frames of the target area captured from different perspectives. The method further includes performing an initial catheter detection for catheter tip candidates in each 2D frame of the fluoroscopic data, performing a secondary catheter detection for catheter tip candidates in each 2D frame of the fluoroscopic data. Additionally, the method includes eliminating false-positive catheter tip candidates of the secondary catheter detection by reconstructing a 3D position of the catheter tip and finding an intersecting point of rays corresponding to each 2D frame, and reweighing the catheter tip candidates of the secondary catheter detection based on a distance of the catheter tip candidate from a projected 3D point.

The initial catheter detection may include applying a shallow neural network operator and the secondary catheter detection may include applying a deep neural network operator. The secondary catheter detection for catheter tip candidates in each 2D frame of the fluoroscopic data may include considering the catheter tip candidates of the initial catheter detection. Reweighing the catheter tip candidates of the secondary catheter detection based on a distance of the catheter tip candidate from a projected 3D point may include decreasing a weight of a pixel corresponding to a candidate when the distance of the catheter tip candidate is far from the projected 3D point.

Additionally, the method may further include iteratively repeating eliminating false-positive detections by reconstructing a 3D position of the catheter tip and finding an intersecting point of rays corresponding to each 2D frame. Additionally, or alternatively, the method may include displaying a user interface for manually selecting the catheter tip in a 2D fluoroscopic frame of the fluoroscopic data prior to performing an initial catheter detection for catheter tip candidates in each 2D frame of the fluoroscopic data.

In another aspect, a method for detecting a catheter in fluoroscopic data during a surgical navigation procedure is provided. The method includes tracking an electromagnetic position of a catheter using electromagnetic coordinates during a navigation procedure of the catheter to a target area, displaying the tracked electromagnetic position of the catheter on a display of a 3D rendering, and acquiring fluoroscopic data from a fluoroscopic sweep of the target area. The fluoroscopic data includes 2D fluoroscopic frames of the target area captured from different perspectives. The target area may be, for example, within a patient's luminal network and the 3D rendering may be, for example, a 3D rendering of the patient's luminal network. The method further includes constructing fluoroscopic-based three dimensional volumetric data of the target area from the acquired fluoroscopic data including a three-dimensional construction of a soft-tissue target in the target area, acquiring, for each 2D frame of the fluoroscopic data, data of a position of the catheter relative to the three-dimensional construction of the soft-tissue, and registering the acquired data of the position of the catheter relative to the three-dimensional construction of the soft-tissue with the electromagnetic position of the catheter. Additionally, the method includes displaying the position of the catheter on the display of the 3D rendering based on the registration of the acquired data of the position of the catheter relative to the three-dimensional construction of the soft-tissue with the electromagnetic position of the catheter.

The method may further include performing at least one catheter detection for catheter tip candidates in each 2D frame of the fluoroscopic data. An initial catheter detection may include applying a shallow neural network operator and a secondary catheter detection may include applying a deep neural network operator. Additionally, or alternatively, the method may further include eliminating false-positive catheter tip candidates of the secondary catheter detection by reconstructing a 3D position of the catheter tip and finding an intersecting point of rays corresponding to each 2D frame. The secondary catheter tip detection may consider the candidates identified in the initial catheter detection. Additionally, or alternatively, the method may include reweighing the catheter tip candidates of the secondary catheter detection based on a distance of the catheter tip candidate from a projected 3D point.

In another aspect, a system for performing an electromagnetic surgical navigation procedure is provided. The system includes an electromagnetic tracking system having electromagnetic tracking coordinates, a catheter including a sensor configured to couple to the electromagnetic tracking system for detecting a position of the catheter in the electromagnetic coordinates, and a computing device operably coupled to the electromagnetic tracking system and the catheter.

The computing device is configured to display a navigation path to guide navigation of the catheter to a target area, display the position of the catheter in the electromagnetic coordinates on a 3D rendering, and acquire fluoroscopic data from a fluoroscopic sweep of the target area. The target area may be, for example, within a patient's luminal network and the 3D rendering may be, for example, a 3D rendering of the patient's luminal network. The fluoroscopic data includes 2D fluoroscopic frames of the target area captured from different perspectives. Additionally, the computing device is configured to perform an initial catheter detection for catheter tip candidates in each 2D frame of the fluoroscopic data, perform a secondary catheter detection for catheter tip candidates in each 2D frame of the fluoroscopic data, eliminate false-positive catheter tip candidates of the secondary catheter detection by reconstructing a 3D position of the catheter tip and finding an intersecting point of rays corresponding to each 2D frame, and reweigh the catheter tip candidates of the secondary catheter detection based on a distance of the catheter tip candidate from a projected 3D point.

The computing device may be configured to perform an initial catheter detection for catheter tip candidates in each 2D frame of the fluoroscopic data by applying a shallow neural network operator and perform a secondary catheter detection for catheter tip candidates in each 2D frame of the fluoroscopic data by applying a deep neural network operator. Additionally, or alternatively, the computing device may be configured to construct fluoroscopic-based three dimensional volumetric data of the target area from the acquired fluoroscopic data. The fluoroscopic-based three dimensional volumetric data includes a three-dimensional construction of a soft-tissue target in the target area.

In an aspect, the computing device is further configured to acquire, for each 2D frame of the fluoroscopic data, data of a position of the catheter relative to the three-dimensional construction of the soft-tissue, register the acquired data of the position of the catheter relative to the three-dimensional construction of the soft-tissue with the electromagnetic position of the catheter, and display the position of the catheter on the display of the 3D rendering based on the registration of the acquired data of the position of the catheter relative to the three-dimensional construction of the soft-tissue with the electromagnetic position of the catheter.

BRIEF DESCRIPTION OF THE DRAWINGS

Various aspects and embodiments of the disclosure are described hereinbelow with references to the drawings, wherein.

DETAILED DESCRIPTION

In order to navigate tools to a remote soft-tissue target for biopsy or treatment, both the tool and the target should be visible in some sort of a three dimensional guidance system. The majority of these systems use some X-ray device to see through the body. For example, a CT machine can be used with iterative scans during procedure to provide guidance through the body until the tools reach the target. This is a tedious procedure as it requires several full CT scans, a dedicated CT room and blind navigation between scans. In addition, each scan requires the staff to leave the room. Another option is a Cone-beam CT machine which is available in some operation rooms and is somewhat easier to operate, but is expensive and like the CT only provides blind navigation between scans, requires multiple iterations for navigation and requires the staff to leave the room.

Accordingly, there is a need for a system that can achieve the benefits of the CT and Cone-beam CT three dimensional image guidance without the underlying costs, preparation requirements, and radiation side effects associated with these systems.

The disclosure is directed to a system and method for catheter detection in fluoroscopic data and constructing local three dimensional volumetric data, in which small soft-tissue objects are visible, from the fluoroscopic data captured by a standard fluoroscopic imaging device available in most procedure rooms. The catheter detection and constructed fluoroscopic-based local three dimensional volumetric data may be used for guidance, navigation planning, improved navigation accuracy, navigation confirmation, and treatment confirmation.

Figure 1:
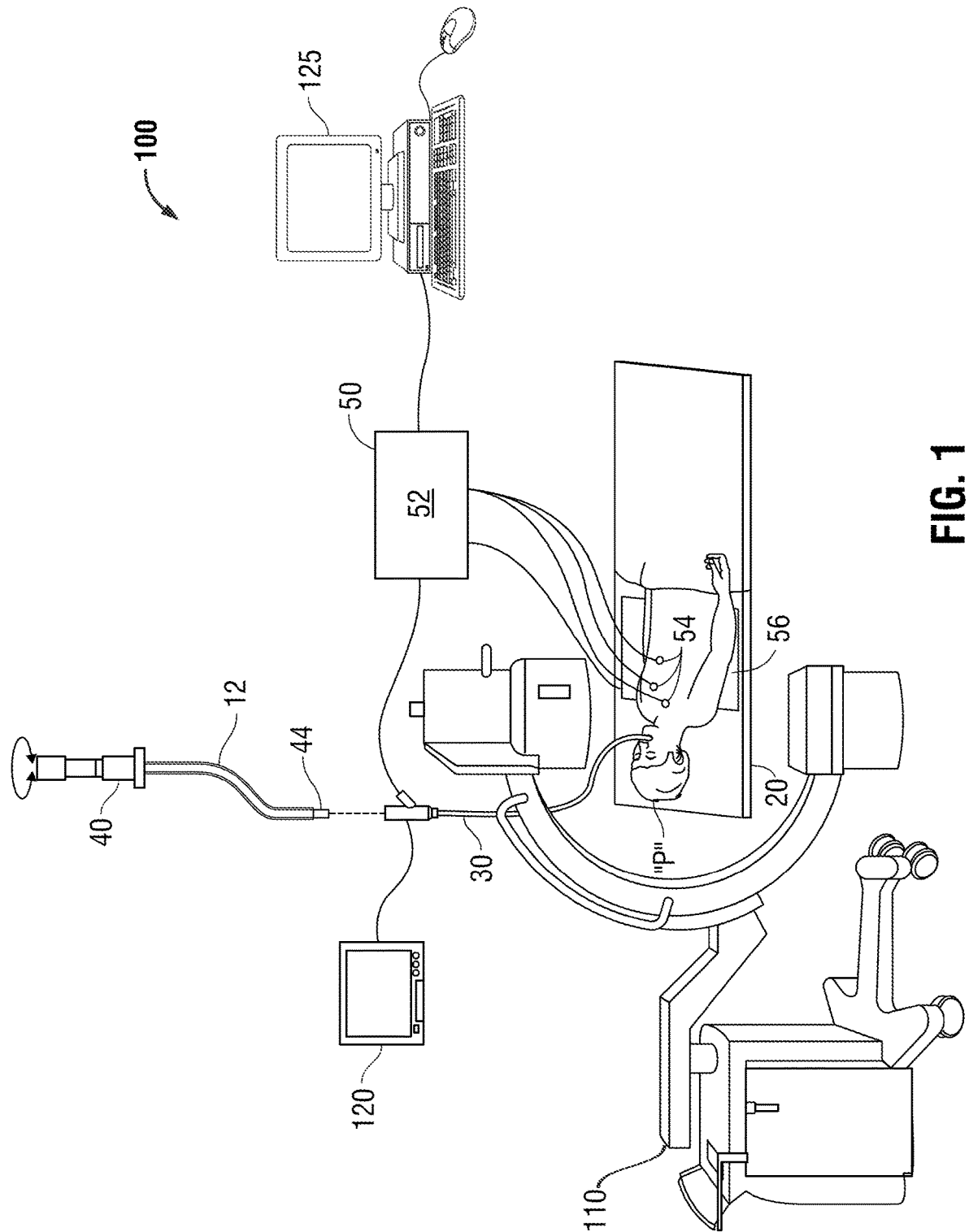
FIG. 1 is a perspective view of one illustrative embodiment of an electromagnetic navigation (EMN) system incorporating a fluoroscopic imaging device in accordance with the disclosure.

FIG. 1 depicts an Electromagnetic Navigation (EMN) system 100 configured for reviewing CT image data to identify one or more targets, planning a pathway to an identified target (planning phase), navigating an extended working channel (EWC) 12 of a catheter guide assembly 40 to a target (navigation phase) via a user interface, and confirming placement of the EWC 12 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical instrument, such as a biopsy tool or other tool, may be inserted into the EWC 12 to obtain a tissue sample (or perform any treatment) from the tissue located at, or proximate to, the target.

As shown in FIG. 1, EWC 12 is part of a catheter guide assembly 40. In practice, the EWC 12 is inserted into bronchoscope 30 for access to a luminal network of the patient "P." Specifically, EWC 12 of catheter guide assembly 40 may be inserted into a working channel of bronchoscope 30 for navigation through a patient's luminal network. A distal portion of the EWC 12 includes a sensor 44. The position and orientation of the sensor 44 relative to the reference coordinate system, and thus the distal portion of the EWC 12, within an electromagnetic field can be derived. Catheter guide assemblies 40 are currently marketed and sold by Medtronic PLC under the brand names SUPERDIMENSION® Procedure Kits, or EDGE™ Procedure Kits, and are contemplated as useable with the disclosure. For a more detailed description of the catheter guide assemblies 40, reference is made to commonly-owned U.S. Pat. No. 9,247,992, filed on Mar. 15, 2013, by Ladtkow et al, U.S. Pat. Nos. 7,233,820, and 9,044,254, the entire contents of each of which are hereby incorporated by reference. System 100 and its components are described in greater detail below.

The following description of FIGS. 2-7 provides an exemplary workflow of using the components of system 100, including the computing device 125 and the fluoroscopic imaging device 110, to accurately detect a catheter in the fluoroscopic data (for example, by eliminating any false-positive detections). Additionally, the following description of FIGS. 2-7 provides an exemplary workflow of using system 100 to construct local, fluoroscopic-based, three dimensional volumetric data of a desired region of interest, register the position of the detected catheter relative to a target with an electromagnetic coordinate system tracking the catheter, and update a displayed position of the catheter relative to the target using the registration. The systems and methods described herein may be useful for visualizing a particular target region of a patient utilizing imaging devices which are commonly located within a surgical setting during EMN procedures, thereby obviating the need for subsequent MRI or CT scans, and confirming the placement of the catheter relative to the target by providing an updated and more accurate display of the catheter in a 3D rendering of a patient's luminal network.

Figure 2:
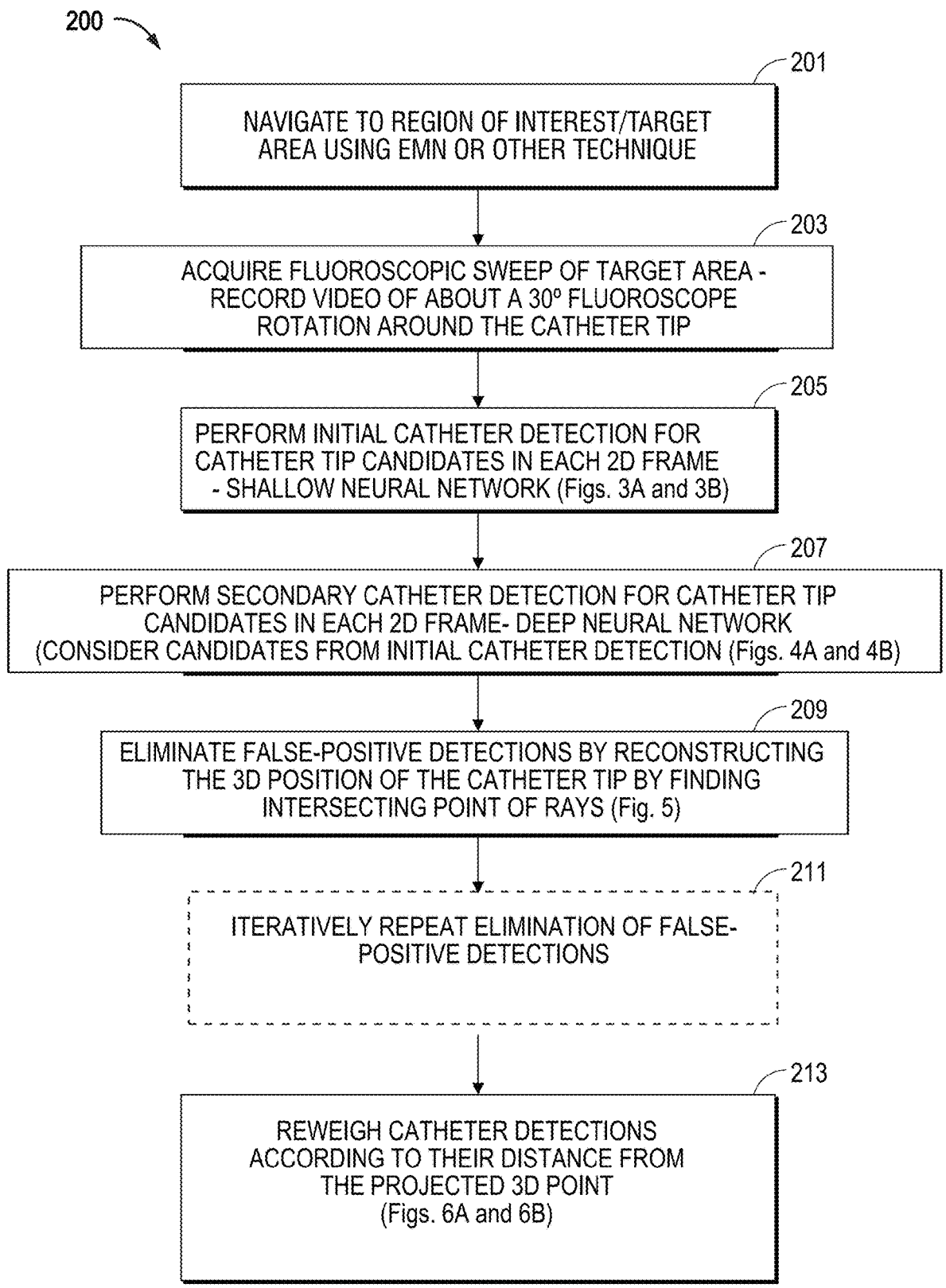
FIG. 2 is a flow chart of a method for detecting a catheter in fluoroscopic data and eliminating false-positive detections.

FIG. 2 illustrates a method for detecting a catheter in fluoroscopic data and eliminating false-positive detections in conjunction with a system such as the system 100 described in FIG. 1 which will now be described with particular detail. Although the methods illustrated and described herein are illustrated and described as being in a particular order and requiring particular steps, any of the methods may include some or all of the steps and may be implemented in any order. Additionally, any or all of the steps of any of the methods described herein may be carried out by computing device 125 of system 100 or any other component or combination of components of system 100.

Method 200 begins with step 201, where a catheter (or any surgical tool) is navigated to a region of interest within a patient's luminal network. The navigation in step 201 may utilize the electromagnetic tracking and pathway plans described above. In step 203, a fluoroscopic sweep of the target area is performed to acquire fluoroscopic data of the target area with the catheter positioned therein. In particular, in step 203, a fluoroscope is positioned about the patient such that fluoroscopic images of the target area may be captured along the entire sweep (e.g. ranging from the angles of −30 degrees and +30 degrees).

Figure 3A:
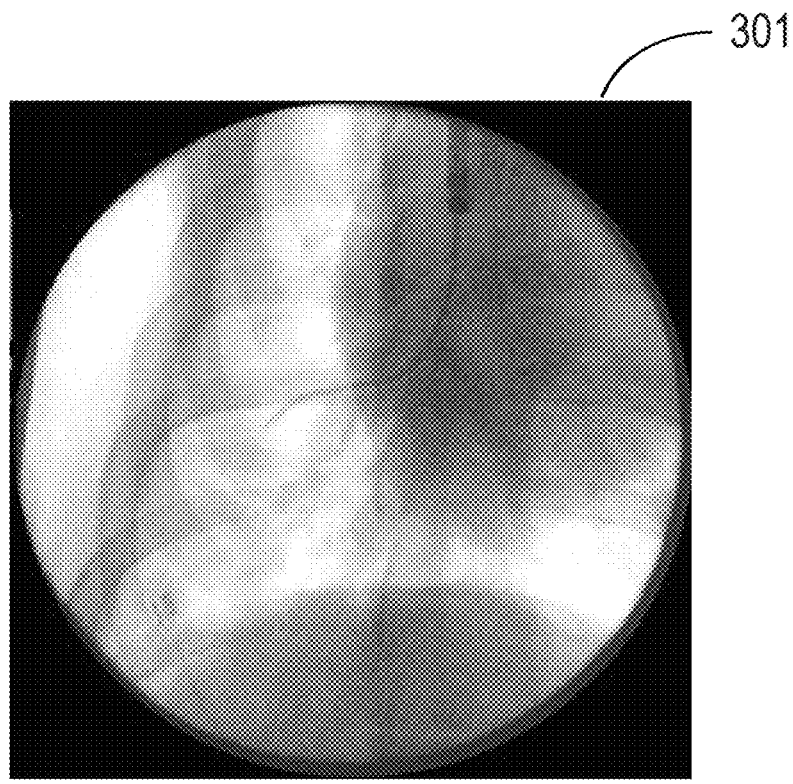
FIG. 3A is an illustration of an example of a frame of fluoroscopic data captured by a fluoroscopic imaging device showing an extended working channel of a catheter assembly positioned within a target region of a patient in accordance with the instant disclosure.
Figure 3B:
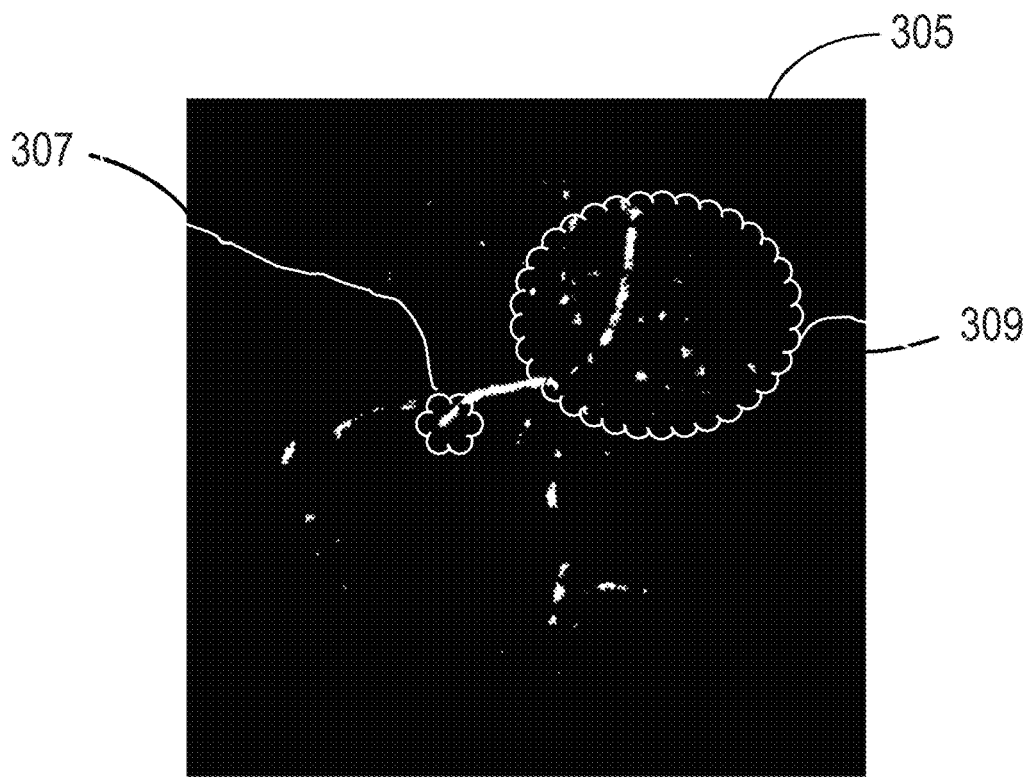
FIG. 3B is an illustration of a resulting image after an initial catheter detection operator is performed on the frame of FIG. 3A.

After the fluoroscopic data is acquired, in step 205 an initial catheter detection is performed. In the initial catheter detection, computing device performs an operator in each 2D frame of the fluoroscopic data to detect possible catheter tip candidates in each 2D frame. In one aspect, step 205 includes utilizing a shallow neural network operator (e.g., four layers). Utilizing the shallow neural network operator provides the advantage of fast completion (approximately 1 second for every 32 2D frames of the fluoroscopic data), but simultaneously provides the disadvantage of identifying many false-positive catheter tip detections. In particular, FIG. 3A illustrates an example 2D frame 301 of fluoroscopic data before a shallow neural network operator is applied in step 205, and FIG. 3B illustrates the resulting image 305 after the shallow neural network operator is applied in step 205 showing all of the catheter tip candidates detected. As seen in FIG. 3B, while the true catheter tip 307 in the frame has been detected as a candidate, many false-positive 309 candidate detections have been made as well.

Figure 4A:
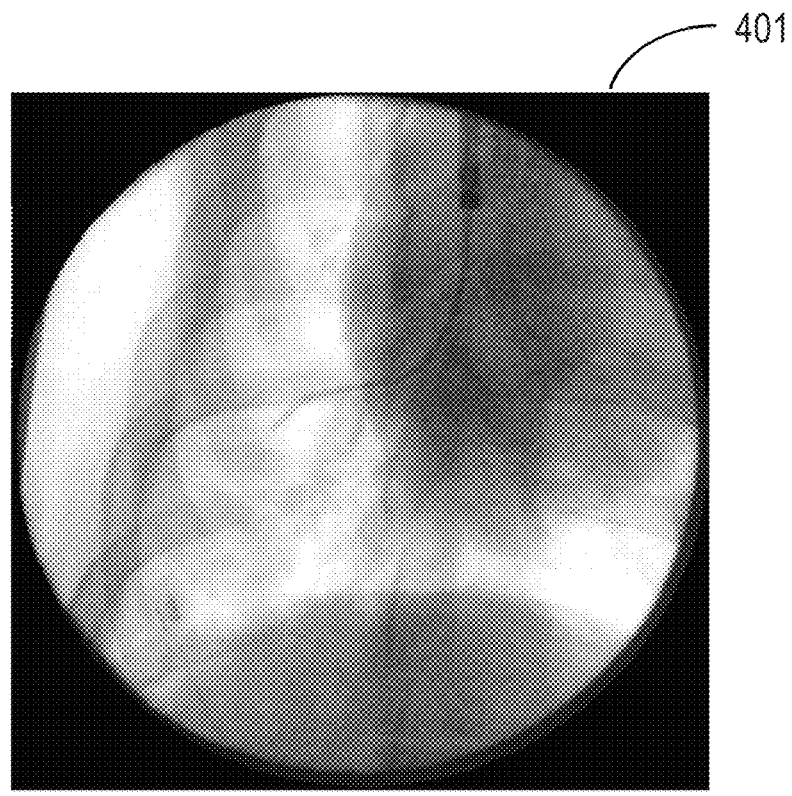
FIG. 4A is an illustration of an example of a frame of a fluoroscopic data captured by a fluoroscopic imaging device showing an extended working channel of a catheter assembly positioned within a target region of a patient in accordance with the instant disclosure.
Figure 4B:
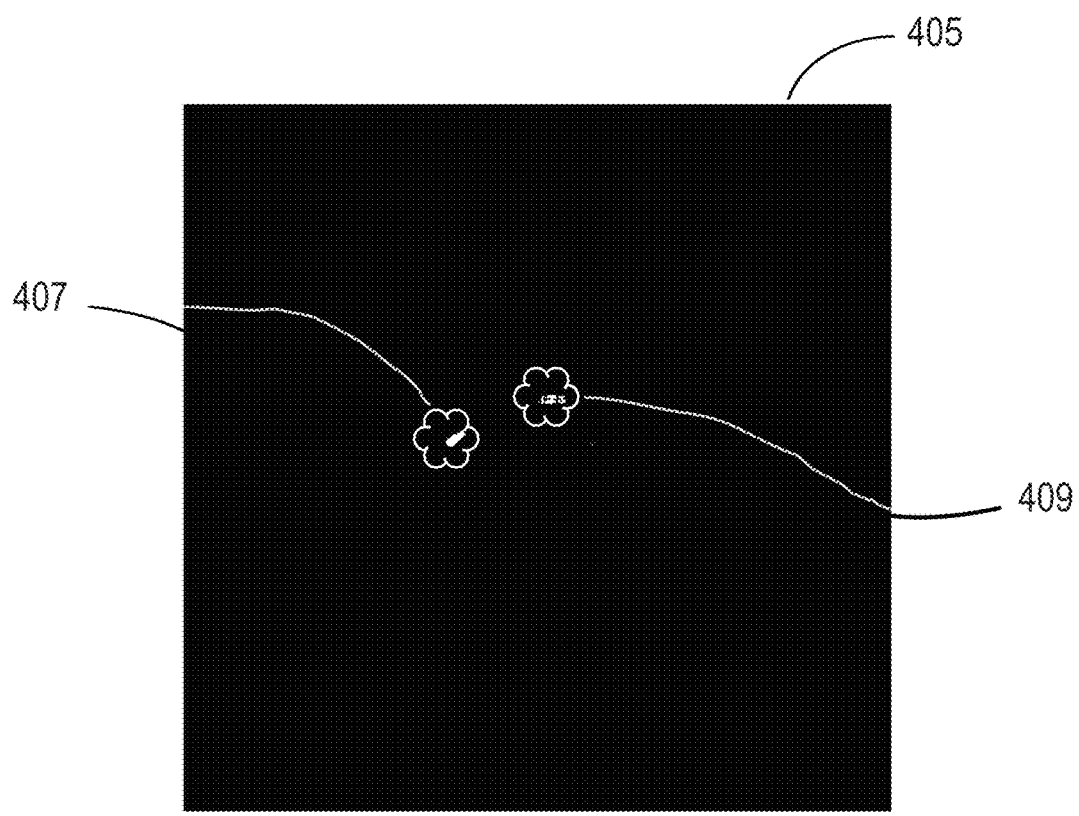
FIG. 4B is an illustration of a resulting image after secondary catheter detection operator is performed on the frame of FIG. 4A.
Figure 5:
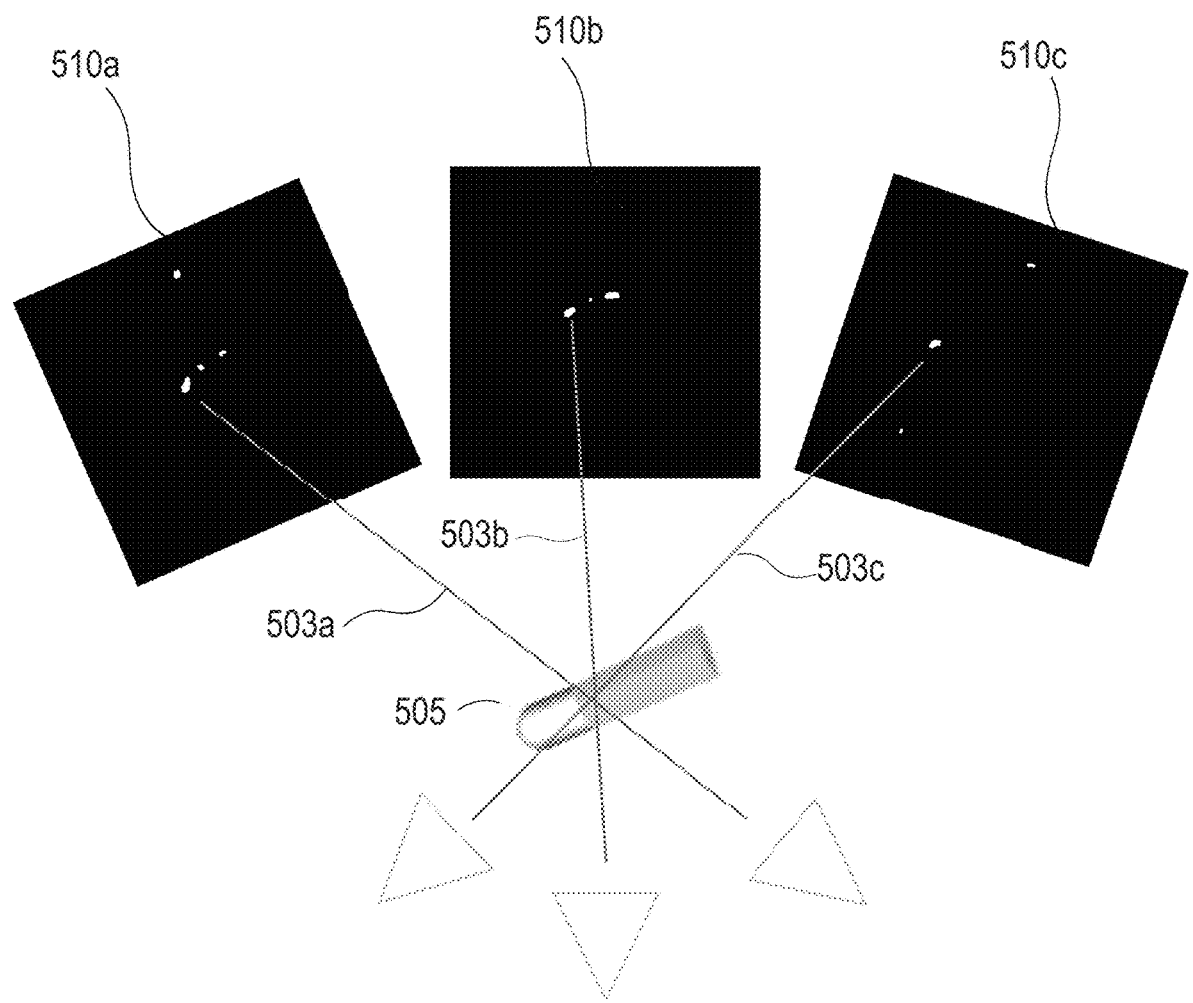
FIG. 5 is an illustration of resulting image frames of fluoroscopic data, after undergoing initial and secondary catheter detection operators, and respective rays of each resulting frame intersecting at a common intersecting point.

In step 207, a secondary catheter detection operation is performed to detect catheter tip candidates in each 2D frame of the fluoroscopic data. In one aspect, step 207 includes utilizing a second neural network operator, in this case a deep neural network operator (e.g., eleven layers). Utilizing the deep neural network operator takes a longer period of time to complete when compared to the shallow neural network operator, but results in fewer false-positive candidate detections. Additionally, the deep neural network operator alone, though not providing as many false-positive candidate detections as the shallow neural network operator, in some instances fails to detect the actual catheter tip as a candidate. FIG. 4A illustrates an example 2D frame 401 of fluoroscopic data before a deep neural network operator is applied in step 207, and FIG. 4B illustrates the resulting image 405 after the deep neural network operator is applied in step 207. As seen in FIG. 4B, the true catheter tip 407 in the image has been detected as a candidate and only few false-positive 409 candidate detections have been made.

In view of the above, one benefit of the disclosed method is that utilizing only one of the initial catheter detection in step 205 or the secondary catheter detection in step 207 could be insufficient for accurately identifying the catheter tip in the fluoroscopic data. As explained above, if the shallow neural network operator of step 205 were performed alone, the catheter will be detected in almost all of the 2D frames, but many false-positives will be detected as well, leading to an inaccurate catheter detection. Additionally, if the deep neural network operator were performed alone, then few false positives will be detected, but some actual catheter detections will be missed, also leading to an inaccurate catheter detection. Accordingly, method 200 includes applying both the shallow neural network operator and the deep neural network operator to ensure an accurate catheter detection. Additionally, if the deep neural network has a misdetection in a fluoro video frame, the catheter won't be detected in that frame (even if it was found in the initial catheter detection). Thus, one thing that prevents misdetection of the catheter in this case are valid detections from other frames, as described in further detail below. Another benefit of utilizing two separate neural networks is that splitting the detector to an initial network and a second deeper network is may enhance runtime optimization as described above.

In one aspect, in step 207, the deep neural network operator considers the candidates from the initial catheter detection of step 205. That is, in utilizing the candidates detected in the initial catheter detection, it can be ensured that the actual catheter will not be missed in the deep neural network operator and will always be identified as a catheter candidate after performance of the secondary catheter detection. In particular, the initial catheter detection outputs a "catheter probability" for each pixel in each fluoroscopic frame. Only pixels with high probability (above some fixed threshold) are considered as catheter candidates after the initial catheter detection. An image patch is extracted around each pixel candidate (having the catheter probability exceeding the threshold) and is input to the second catheter detection (e.g., the deep neural network).

In step 209, false-positive detections are eliminated by reconstructing 3D position of the catheter tip. In particular, with reference to FIG. 5, the intersecting point 505 of the rays 503a, 503b, 503c . . . 503n extending from the candidates of each 2D frame 501a, 501b, 501c . . . 501n is the 3D reconstructed position of the catheter tip. In step 209, when the number of rays intersecting at the same point for a particular catheter candidate exceeds a preconfigured threshold, it is determined that the candidate is not a false-positive and is actually the catheter tip. In particular, in order to confirm that the candidate is not a false-positive detection, a certain numbers of rays must be intersecting at the same intersection point. When the number of rays intersecting at the same point for a particular catheter candidate is below a preconfigured threshold, then it is determined that the candidate is a false-positive detection and not the catheter tip. Method 200 may optionally also include step 211, where the process of eliminating false-positive candidate detections is iteratively repeated. Iteratively repeating the elimination of false-positive candidate detections in step 211, enables the preconfigured threshold for intersecting rays to be set at an optimal value, leading to more reliable and accurate elimination of false-positive candidate detections.

Figure 6A:
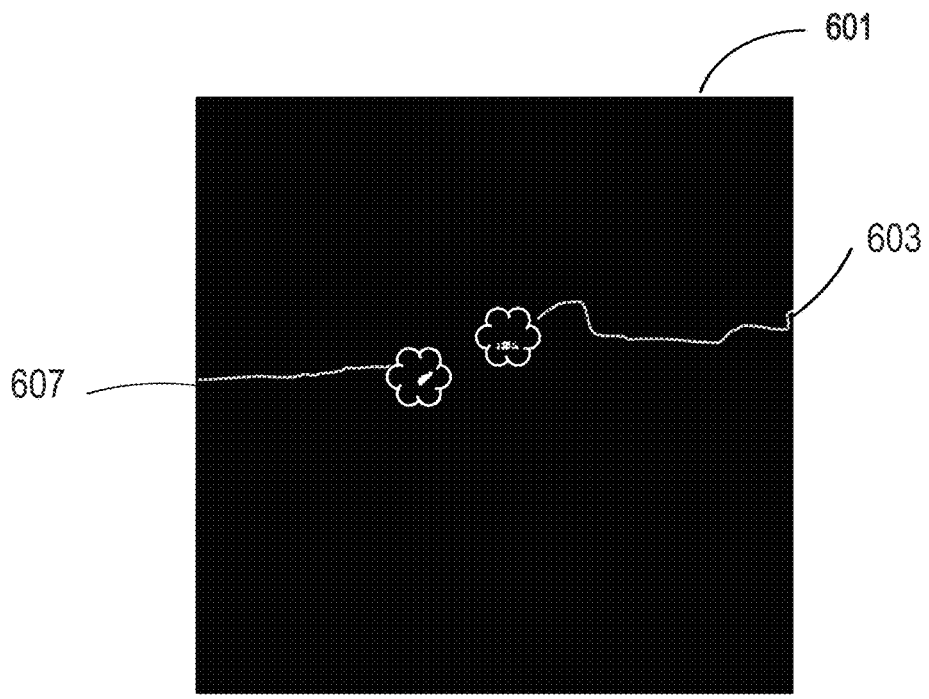
FIG. 6A is an illustration of a resulting image after an initial 3D reconstruction of a 3D position of a catheter tip.
Figure 6B:
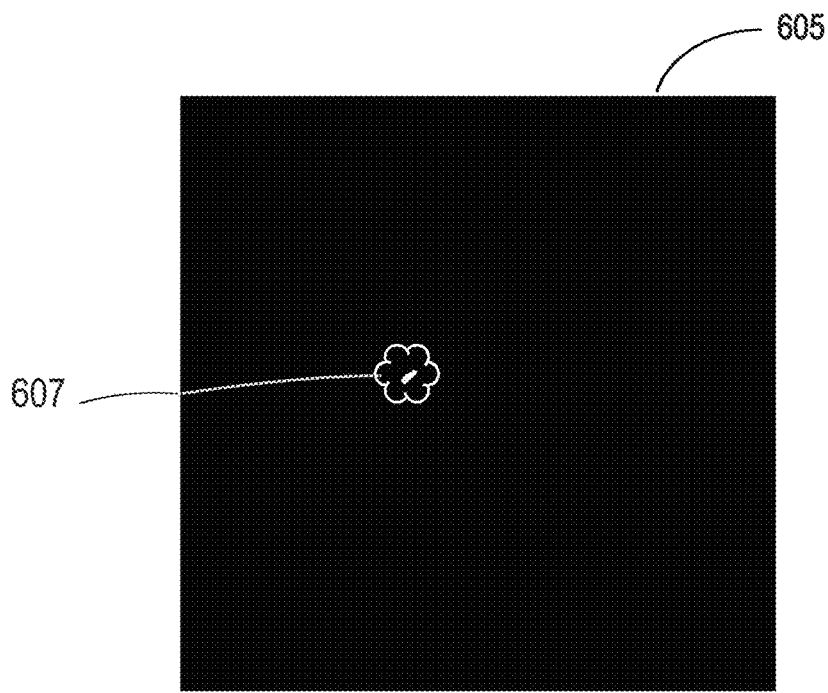
FIG. 6B is an illustration of a resulting image after a 2D detections of the catheter tip of FIG. 6A are reweighted.

In step 213, the catheter candidate detections are reweighed according to their distance from the projected 3D point in step 209. In particular, with reference to FIGS. 6A and 6B, FIG. 6A illustrates an example image 601 after steps 205-209 are completed and FIG. 6B illustrates an image 605 after the reweighing of step 213 in performed. The image 601 in FIG. 6A includes as catheter tip candidates, the actual catheter tip 607 and a false-positive 603. The image 605 in FIG. 6B includes only the actual catheter tip 607 as a candidate and does not include any false-positives. In step 213, each voxel is assigned a weight according to the number of rays intersecting through the voxel and the distance of the voxel from the 3D position of the catheter tip identified in step 209. In step 213, any candidate that is far in distance from the 3D position of the catheter tip identified in step 209 will be assigned a lower weight and will be identified as a false-positive candidate detection and will be removed. On the other hand, any candidate that is close in distance to the 3D position of the catheter tip identified in step 209 will be assigned a higher weight and will be identified as a catheter tip candidate detection and will remain.

Figure 7:
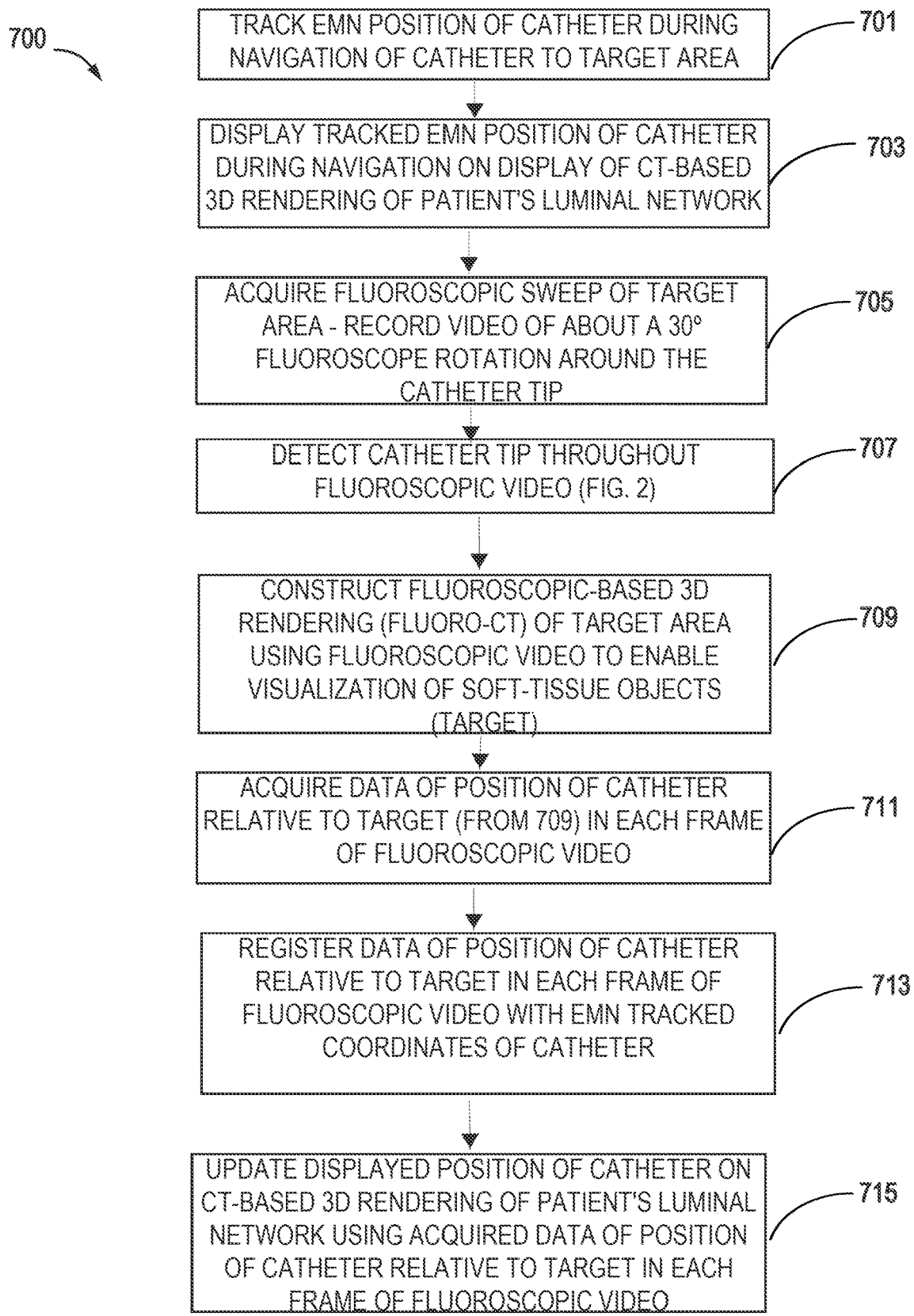
FIG. 7 is a flow chart of a method for updating the position of a navigated catheter relative to a target on a 3D rendering of a patient's luminal network.

FIG. 7 illustrates a method for performing an electromagnetic surgical navigation procedure in conjunction with a system such as the system 100 described in FIG. 1 utilizing method 200, which will now be described with particular detail and will be referred to as method 700. Although the methods illustrated and described herein are illustrated and described as being in a particular order and requiring particular steps, any of the methods may include some or all of the steps and may be implemented in any order. Additionally, any or all of the steps of any of the methods described herein may be carried out by computing device 125 of system 100 or any other component or combination of components of system 100.

Method 700 begins at step 701 where the electromagnetic position of a catheter is tracked during navigation of the catheter to a target area within a patient's luminal network. In step 703, the tracked electromagnetic position of the catheter is displayed during the navigation on a display of a CT-based 3D rendering of the patient's luminal network. Displaying the electromagnetic position of the catheter on the 3D rendering of the patient's luminal network assists the clinician in navigating to the region of interest or target area. Step 703 may additionally include displaying a predetermined route or path to follow through the patient's luminal network to navigate to the target area. Such a display of the pathway or route enables a clinician to identify when the catheter has deviated from the desired path, the progress of the navigation, and when the target is reached.

Once the catheter is navigated to the target area as displayed in step 703, it is possible that the actual position of the catheter within the patient's luminal network is not exactly as displayed in step 703, because the displayed position of the catheter is based only on the electromagnetically tracked position of the catheter's sensor and is displayed over an old CT-data set. Targets within the target area, and other such anatomical features, may have changed since the time of acquisition of the CT data and the electromagnetic tracking is subject to interference and unreliability. Additionally, the display in step 703 merely shows a representation of the catheter, and not the actual catheter within the luminal network relative to structures therein. To more accurately display the actual position of the catheter within the patient's actual luminal network, method 700 proceeds to step 705.

In step 705, a fluoroscopic sweep of the target area is performed to acquire fluoroscopic data of the target area with the catheter positioned therein. In particular, in step 705, a fluoroscope is positioned about the patient such that fluoroscopic images of the target area may be captured along a sweep (e.g. ranging from the angles of −30 degrees and +30 degrees). In step 707, the catheter tip is detected throughout the frames of the fluoroscopic data. In one aspect, step 707 utilizes some or all of the steps of method 200 for the catheter detection.

In step 709, a fluoroscopic-based 3D rendering of the target area with the catheter positioned therein is constructed. Such a fluoroscopic-based 3D construction enables visualization of objects that are not otherwise visible in the fluoroscopic data itself. For example, small soft-tissue objects, such as tumors or lesions, are not visible in the fluoroscopic data, but are visible in the fluoroscopic-based 3D rendering of the target area. Further details regarding the construction of step 709 may be found in U.S. Patent Application Publication No. 2017/0035380, filed Aug. 1, 2016, entitled System and Method for Navigating to Target and Performing Procedure on Target Utilizing Fluoroscopic-Based Local Three Dimensional Volume Reconstruction, and U.S. Patent Application Publication No. 2017/0035379, filed Aug. 1, 2016, entitled System and Method for Local Three Dimensional Volume Reconstruction Using a Standard Fluoroscope, the entire contents of each of which are incorporated by reference herein.

In step 711, position data of the catheter relative to the target in the target area in each frame of the fluoroscopic data is acquired. In particular, the construction of the fluoroscopic-based 3D rendering in step 709 enables the visibility of the target (e.g., soft tissue object, lesion, tumor, etc.) and the location of the target to be determined or otherwise ascertained. As described above, prior to the construction of the fluoroscopic-based 3D rendering in step 709, the soft-tissue objects (e.g., target, tumor, lesion, etc.) are not visible and the location of the object(s), relative to the catheter cannot be determined. In one aspect, in step 711, the position, orientation, and distance of the catheter relative to the target are determined for each slice of the fluoroscopic-based 3D rendering. Additionally, the position data acquired in step 711 may be correlated to the fluoroscopic data acquired in step 705.

In step 713, the position data acquired in step 711 is registered to the electromagnetic tracked coordinates of the catheter. In one aspect, in step 713, the system displays the catheter on the CT data by employing an "Antenna-to-CT" registration, where the catheter position (and optionally orientation) in antenna coordinates is continuously calculated by the electromagnetic localization algorithms. The position is then transformed to CT coordinates. This registration may be based on the first bifurcations of the airway tree (main carina and bronchi). Due to this (and other factors, such as patient sedation, and different patient pose during CT and bronchoscopic procedure) the registration is less accurate in the periphery of the lungs. The registration is corrected for the target area by composing one or more of the following registrations: 1) Antenna-to-fluoro, where the catheter position is known in both antenna coordinates (using electromagnetic localization) and fluoro coordinates (automatic catheter detection described in the preceding steps), and is used as a basis for the registration; and/or 2) Fluoro-to-CT, where the target's position is marked on the CT data pre-operatively and then also marked on the fluoro-based 3D reconstruction inter-operatively. After performing calculations for the above registrations, a new catheter position in antenna coordinates is transformed to fluoro coordinates by employing the "Antenna-to-fluoro" registration, which is then transformed to CT coordinates by employing the "Fluoro-to-CT" registration.

In step 715, the displayed position of the catheter on the CT-based 3D rendering of the patient's luminal network is updated using the position data acquired in step 711. In particular, the position, orientation, and distance of the catheter relative to the target in the fluoroscopic-based 3D data set are compared to the position, orientation, and distance of the displayed catheter relative to the target in the CT-based 3D rendering. In one aspect, the orientation, position, and distance of the displayed catheter relative to the target in the CT-based rendering is updated to correspond or match with the orientation, position, and distance of the catheter relative to the target in the fluoroscopic-based 3D data set.

Referring back to FIG. 1, EMN system 100 generally includes an operating table 20 configured to support a patient "P;" a bronchoscope 30 configured for insertion through the patient's "P's" mouth into the patient's "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54 and a transmitter mat 56; and a computing device 125 including software and/or hardware used to facilitate identification of a target, pathway planning to the target, navigation of a medical instrument to the target, and confirmation of placement of an EWC 12, or a suitable device therethrough, relative to the target.

A fluoroscopic imaging device 110 capable of acquiring fluoroscopic or x-ray images or video of the patient "P" is also included in this particular aspect of system 100. The fluoroscopic data (e.g., images, series of images, or video) captured by the fluoroscopic imaging device 110 may be stored within the fluoroscopic imaging device 110 or transmitted to computing device 125 for storage, processing, and display. Additionally, the fluoroscopic imaging device 110 may move relative to the patient "P" so that images may be acquired from different angles or perspectives relative to the patient "P" to create a fluoroscopic video from a fluoroscopic sweep. Fluoroscopic imaging device 110 may include a single imaging device or more than one imaging device. In embodiments including multiple imaging devices, each imaging device may be a different type of imaging device or the same type. Further details regarding the imaging device 110 are described in U.S. Pat. No. 8,565,858, which is incorporated by reference in its entirety herein.

Computing device 125 may be any suitable computing device including a processor and storage medium, wherein the processor is capable of executing instructions stored on the storage medium. The computing device 125 may further include a database configured to store patient data, CT data sets including CT images, fluoroscopic data sets including fluoroscopic images and video, navigation plans, and any other such data. Although not explicitly illustrated, the computing device 125 may include inputs, or may otherwise be configured to receive, CT data sets, fluoroscopic images/video and other data described herein. Additionally, computing device 125 includes a display configured to display graphical user interfaces.

With respect to the planning phase, computing device 125 utilizes previously acquired CT image data for generating and viewing a three dimensional model of the patient's "P's" airways, enables the identification of a target on the three dimensional model (automatically, semi-automatically, or manually), and allows for determining a pathway through the patient's "P's" airways to tissue located at and around the target. More specifically, CT images acquired from previous CT scans are processed and assembled into a three dimensional CT volume, which is then utilized to generate a three dimensional model of the patient's "P's" airways. The three dimensional model may be displayed on a display associated with computing device 125, or in any other suitable fashion. Using computing device 125, various views of the three dimensional model or enhanced two dimensional images generated from the three dimensional model are presented. The enhanced two dimensional images may possess some three dimensional capabilities because they are generated from three dimensional data. The three dimensional model may be manipulated to facilitate identification of target on the three dimensional model or two dimensional images, and selection of a suitable pathway (e.g., route to be following during navigation) through the patient's "P's" airways to access tissue located at the target can be made. Once selected, the pathway plan, three dimensional model, and images derived therefrom, can be saved and exported to a navigation system for use during the navigation phase(s). One such planning software is the ILOGIC® planning suite currently sold by Medtronic PLC.

With respect to the navigation phase, a six degrees-of-freedom electromagnetic tracking system 50, e.g., similar to those disclosed in U.S. Pat. Nos. 8,467,589, 6,188,355, and published PCT Application Nos. WO 00/10456 and WO 01/67035, the entire contents of each of which are incorporated herein by reference, or other suitable positioning measuring system, is utilized for performing registration of the images and the pathway for navigation, although other configurations are also contemplated. Tracking system 50 includes a tracking module 52, a plurality of reference sensors 54, and a transmitter mat 56. Tracking system 50 is configured for use with a sensor 44 of catheter guide assembly 40 to track the electromagnetic position thereof within an electromagnetic coordinate system.

Transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. One or more of reference sensors 54 are attached to the chest of the patient "P." The six degrees of freedom coordinates of reference sensors 54 are sent to computing device 125 (which includes the appropriate software) where they are used to calculate a patient coordinate frame of reference. Registration, as detailed below, is generally performed to coordinate locations of the three dimensional model and two dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Further details of such a registration technique and their implementation in luminal navigation can be found in U.S. Patent Application Publication No. 2011/0085720, the entire content of which is incorporated herein by reference, although other suitable techniques are also contemplated.

Registration of the patient's "P's" location on the transmitter mat 56 is performed by moving sensor 44 through the airways of the patient's "P." More specifically, data pertaining to locations of sensor 44, while EWC 12 is moving through the airways, is recorded using transmitter mat 56, reference sensors 54, and tracking module 52. A shape resulting from this location data is compared to an interior geometry of passages of the three dimensional model generated in the planning phase, and a location correlation between the shape and the three dimensional model based on the comparison is determined, e.g., utilizing the software on computing device 125. In addition, the software identifies non-tissue space (e.g., air filled cavities) in the three dimensional model. The software aligns, or registers, an image representing a location of sensor 44 with a the three dimensional model and two dimensional images generated from the three dimension model, which are based on the recorded location data and an assumption that sensor 44 remains located in non-tissue space in the patient's "P's" airways. Alternatively, a manual registration technique may be employed by navigating the bronchoscope 30 with the sensor 44 to pre-specified locations in the lungs of the patient "P", and manually correlating the images from the bronchoscope to the model data of the three dimensional model.

Following registration of the patient "P" to the image data and pathway plan, a user interface is displayed in the navigation software which sets forth the pathway that the clinician is to follow to reach the target. One such navigation software is the ILOGIC® navigation suite currently sold by Medtronic PLC.

Once EWC 12 has been successfully navigated proximate the target as depicted on the user interface, the EWC 12 is in place as a guide channel for guiding medical instruments including without limitation, optical systems, ultrasound probes, marker placement tools, biopsy tools, ablation tools (i.e., microwave ablation devices), laser probes, cryogenic probes, sensor probes, and aspirating needles to the target.

With the above-described updated position of the catheter relative to a target in a target area, a clinician is able to more accurately navigate to a region of interest or target within a patient's luminal network. Errors in the electromagnetically tracked and displayed location of the catheter in the CT-based 3D rendering of the patient's luminal network are corrected based on near real-time position data extracted from fluoroscopic-based 3D data of target area.

From the foregoing and with reference to the various figure drawings, those skilled in the art will appreciate that certain modifications can also be made to the disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver. Further, the above-described systems and methods are also usable for transthoracic needle aspiration procedures.

Detailed embodiments of the disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and the disclosure is directed to systems and methods that are usable with such instruments and tools. Access to luminal networks may be percutaneous or through natural orifice using navigation techniques. Additionally, navigation through a luminal network may be accomplished using image-guidance. These image-guidance systems may be separate or integrated with the energy device or a separate access tool and may include MM, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for detecting a catheter in fluoroscopic data, the method comprising:
   acquiring fluoroscopic data from a fluoroscopic sweep of a target area, the fluoroscopic data including 2D fluoroscopic frames of the target area captured from different perspectives;
   performing an initial catheter detection for catheter tip candidates in a plurality of 2D frames of the fluoroscopic data;
   performing a secondary catheter detection for catheter tip candidates in the plurality of 2D frames of the fluoroscopic data;
   iteratively determining an intersection point of rays extending from the detected catheter tip candidates in each of the plurality of 2D frames of the second catheter detection; and
   eliminating false-positive catheter tip candidates of the second catheter tip detections whose rays do not pass through the intersection point.

2. The method according to claim 1, wherein performing an initial catheter detection includes applying a shallow neural network operator.

3. The method according to claim 1, wherein performing a secondary catheter detection includes applying a deep neural network operator.

4. The method according to claim 1, further comprising displaying a user interface for manually selecting the catheter tip in a 2D fluoroscopic frame of the fluoroscopic data prior to performing the initial catheter detection for catheter tip candidates in each 2D frame of the fluoroscopic data.

5. The method according to claim 1, further comprising reweighing the catheter tip candidates of the secondary catheter detection based on a distance of the catheter tip candidate from a projected 3D point.

6. The method according to claim 5, wherein reweighing the catheter tip candidates of the secondary catheter detection includes decreasing a weight of a pixel corresponding to a candidate when the distance of the catheter tip candidate is far from the projected 3D point.

7. The method according to claim 1, further comprising constructing a fluoroscopic-based three-dimensional volumetric data of the target area from the acquired fluoroscopic data, the fluoroscopic-based three-dimensional volumetric data including a three-dimensional construction of a soft-tissue target in the target area.

8. A system for performing an electromagnetic surgical navigation procedure, comprising:
   a catheter including a sensor on a distal portion of the catheter;
   a tracking system configured to determine a position and orientation of the distal portion of the catheter;
   a fluoroscope operably coupled to the tracking system; and
   a computing device operably coupled to the tracking system, the fluoroscope, and the catheter, the computing device including a processor and a memory storing thereon instructions, that when executed cause the processor to:

acquire fluoroscopic data from the fluoroscope, the fluoroscopic data including 2D fluoroscopic frames of a target area;
perform an initial catheter detection for catheter tip candidates in a plurality of 2D frames of the fluoroscopic data;
performing a secondary catheter detection for catheter tip candidates in the plurality of 2D frames of the fluoroscopic data;
iteratively determine an intersection point of rays extending from the detected catheter tip candidates in each of the plurality of 2D frames of the second catheter detection; and
eliminate as false-positives the catheter tip candidates of the secondary catheter detections whose rays do not pass through the intersecting point.

9. The system according to claim 8, further comprising the memory storing thereon further instructions, that when executed, cause the processor to perform the initial catheter detection for catheter tip candidates in the plurality of 2D frames of the fluoroscopic data by applying a shallow neural network operator to.

10. The system according to claim 8, further comprising the memory storing thereon further instructions, that when executed, cause the processor to perform the initial catheter detection for catheter tip candidates in the plurality of 2D frames of the fluoroscopic data by applying a deep neural network operator.

11. The system according to claim 8, further comprising the memory storing thereon further instructions, that when executed, cause the processor to display a user interface for manually selecting the catheter tip in a 2D fluoroscopic frame of the fluoroscopic data prior to performing the initial catheter detection for catheter tip candidates in each 2D frame of the fluoroscopic data.

12. The system according to claim 8, further comprising the memory storing thereon further instructions, that when executed, cause the processor to reweigh the catheter tip candidates of the secondary catheter detection based on a distance of the catheter tip candidate from a projected 3D point.

13. The system according to claim 12, further comprising the memory storing thereon further instructions, that when executed, cause the processor to reweigh the catheter tip candidates by decreasing a weight of a pixel corresponding to a candidate when the distance of the catheter tip candidate is far from the projected 3D point.

14. The system according to claim 8, further comprising the memory storing thereon further instructions, that when executed, cause the processor to construct a fluoroscopic-based three-dimensional volumetric data of the target area from the acquired fluoroscopic data, the fluoroscopic-based three-dimensional volumetric data including a three-dimensional construction of a soft-tissue target in the target area.

15. A system for performing an electromagnetic surgical navigation procedure, comprising:
a catheter including a sensor on a distal portion of the catheter;
a tracking system configured to determine a position and orientation of the distal portion of the catheter; and
a computing device operably coupled to the tracking system, a fluoroscope, and the catheter, the computing device including a processor and a memory storing thereon instructions, that when executed, cause the processor to:
acquire fluoroscopic data from a fluoroscopic sweep of a target area, the fluoroscopic data including 2D fluoroscopic frames of the target area captured from different perspectives;
perform an initial catheter detection for catheter tip candidates in a plurality of the 2D frames of the fluoroscopic data;
perform a secondary catheter detection for the catheter tip candidates in the plurality of the 2D frames of the fluoroscopic data;
iteratively determine an intersection point of rays extending from the detected catheter tip candidates in each of the plurality of 2D frames of the second catheter detection; and
eliminate as false positive detections the catheter tip candidates of the secondary catheter detections whose rays do not pass through the intersection point;
construct a fluoroscopic-based three-dimensional volumetric data of the target area from the acquired fluoroscopic data, the fluoroscopic-based three-dimensional volumetric data including a three-dimensional construction of a soft-tissue target in the target area;
identify for each 2D frame of the fluoroscopic data the intersection point as a 3D position of a catheter tip and the intersection points relative to the three-dimensional construction of the soft-tissue target; and
display a position of the catheter tip and the three-dimensional construction of the soft-tissue.

16. The system according to claim 15, further comprising the memory storing thereon further instructions, that when executed, cause the processor to perform the initial catheter detection for the catheter tip candidates in the plurality of 2D frames of the fluoroscopic data by applying a shallow neural network operator.

17. The system according to claim 15, further comprising the memory storing thereon further instructions, that when executed, cause the processor to perform the initial catheter detection for the catheter tip candidates in the plurality of 2D frames of the fluoroscopic data by applying a deep neural network operator.

18. The system according to claim 15, further comprising the memory storing thereon further instructions, that when executed, cause the processor to display a user interface for manually selecting the catheter tip in a 2D fluoroscopic frame of the fluoroscopic data prior to performing the initial catheter detection for catheter tip candidates in each 2D frame of the fluoroscopic data.

19. The system according to claim 15, further comprising the memory storing thereon further instructions, that when executed, cause the processor to reweigh the catheter tip candidates of the secondary catheter tip detection based on a distance of the catheter tip candidate from a projected 3D point.

20. The system according to claim 19, further comprising the memory storing thereon further instructions, that when executed, cause the processor to reweigh the catheter tip candidates by decreasing a weight of a pixel corresponding to a candidate when the distance of the catheter tip candidate is far from the projected 3D point.

* * * * *